US012573241B2

(12) United States Patent
White

(10) Patent No.: US 12,573,241 B2
(45) Date of Patent: Mar. 10, 2026

(54) SYSTEMS AND METHODS FOR SELF MIRROR IMAGE DETECTION

(71) Applicant: CHILD MIND INSTITUTE, INC., New York, NY (US)

(72) Inventor: Curtis P. White, Queens, NY (US)

(73) Assignee: CHILD MIND INSTITUTE, INC., New York, NY (US)

( * ) Notice: Subject to any disclaimer, the term of this patent is extended or adjusted under 35 U.S.C. 154(b) by 408 days.

(21) Appl. No.: 18/362,288

(22) Filed: Jul. 31, 2023

(65) Prior Publication Data

US 2024/0046711 A1 Feb. 8, 2024

Related U.S. Application Data

(60) Provisional application No. 63/394,346, filed on Aug. 2, 2022.

(51) Int. Cl.
| | |
|---|---|
| *G06V 40/60* | (2022.01) |
| *G06V 40/16* | (2022.01) |
| *G16H 20/70* | (2018.01) |

(52) U.S. Cl.
CPC ............ *G06V 40/67* (2022.01); *G06V 40/161* (2022.01); *G16H 20/70* (2018.01)

(58) Field of Classification Search
CPC ...... G06V 40/67; G06V 40/161; G16H 20/70; G16H 10/20; G16H 30/40; G16H 40/63; G16H 50/20
See application file for complete search history.

(56) References Cited

U.S. PATENT DOCUMENTS

| | | | | |
|---|---|---|---|---|
| 2018/0247426 A1* | 8/2018 | Gluck | ................ | G06Q 30/0643 |
| 2019/0050427 A1* | 2/2019 | Wiesel | ..................... | G06T 19/00 |
| 2019/0121221 A1* | 4/2019 | Martí I Renom | .. | G06K 7/10297 |
| 2020/0125647 A1* | 4/2020 | Mintz | .................. | G06V 40/174 |
| 2021/0064910 A1* | 3/2021 | Meier | ....................... | G06T 5/50 |
| 2021/0090209 A1* | 3/2021 | Appleboim | ........ | G06Q 30/0631 |
| 2021/0368093 A1* | 11/2021 | Lee | ...................... | G06V 40/167 |
| 2023/0116629 A1* | 4/2023 | Grymel | .................. | G06N 3/048 |
| | | | | 706/15 |
| 2024/0212272 A1* | 6/2024 | Temple | .............. | G02B 27/0172 |

* cited by examiner

*Primary Examiner* — Wesley J Tucker

(74) *Attorney, Agent, or Firm* — Kelley Drye & Warren LLP; Alan D. Gardner

(57) ABSTRACT

The present invention may be used to determine whether a user of a device, such as a mobile device, is facing a mirror and also pointing their mobile device at an image of themselves in this mirror. The present invention may use machine learning real-time video analysis and/or mobile device sensors to make that determination.

24 Claims, 13 Drawing Sheets

SYSTEMS AND METHODS FOR SELF MIRROR IMAGE DETECTION

BACKGROUND OF THE INVENTION

The benefits of keeping a diary or journal (referred to herein as "journaling") are well established. In addition to overt patient/clinician collaboration, an abundance of evidence has established the benefits of journaling in treatment of depression and anxiety. Intuitively, structured self reflection can be helpful in numerous behavioral health contexts.

Yet, journaling can be difficult for many people, even if it is done in collaboration with a clinician. People who are successful at journaling tend to maintain a journaling routine. They may write (or record audio/video) every morning or every night at or around the same time. They might record journal entries in a specific location, such as in bed or in a particular chair. Establishing a journaling routine, however, can be difficult. In some ways, the pressure to regularly and consistently journal can be so overwhelming that it dissuades people from journaling, or may lead people who have started journaling to stop journaling altogether.

SUMMARY OF THE INVENTION

It is a goal of the present invention to encourage journaling by focusing on visceral real world engagement. Another goal of the present invention is for users to contemplate themselves outside the self-performance demanded by their digitally mediated lives.

The present invention may be used to detect when a user of a device, such as a mobile device, is facing a mirror and also pointing their mobile device at an image of themselves in this mirror (referred to herein a "self mirror image detection") by applying novel real-time video data analysis processes. Facial recognition, or at the very least human head object detection, is common in mobile device software applications. However, existing facial recognition processes cannot determine if the face image is that of a physical person or the mirror image ("self mirror image") of a physical person. The present invention in the above-described context is able to accomplish this distinction through, for example, the application of machine learning real-time video analysis, and/or mobile device sensors.

Numerous variations may be practiced in the preferred embodiment.

BRIEF DESCRIPTION OF THE DRAWINGS

A further understanding of the invention can be obtained by reference to exemplary embodiments set forth in the illustrations of the accompanying drawings. Although the illustrated embodiments are merely exemplary of systems, methods, and apparatuses for carrying out the invention, both the organization and method of operation of the invention, in general, together with further objectives and advantages thereof, may be more easily understood by reference to the drawings and the following description. Like reference numbers generally refer to like features (e.g., functionally similar and/or structurally similar elements).

The drawings are not necessarily depicted to scale; in some instances, various aspects of the subject matter disclosed herein may be shown exaggerated or enlarged in the drawings to facilitate an understanding of different features. Also, the drawings are not intended to limit the scope of this invention, which is set forth with particularity in the claims as appended hereto or as subsequently amended, but merely to clarify and exemplify the invention.

DETAILED DESCRIPTION OF THE INVENTION

Figures 1A, 1B, 1C, 1D, 1E, 1F:
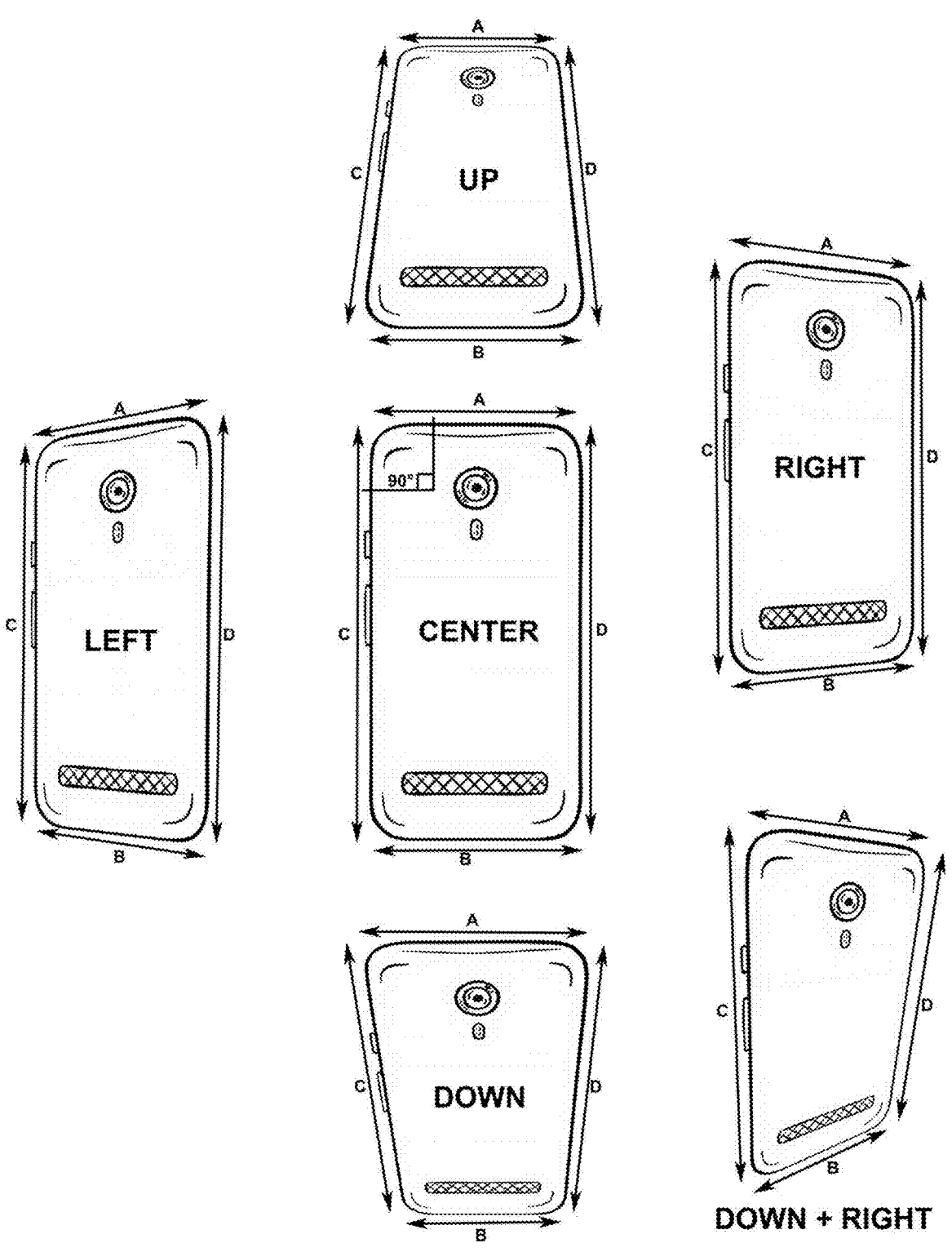
FIGS. 1A-1F depict various geometric appearances of an exemplary mobile device based on orientation of the mobile device.

The invention may be understood more readily by reference to the following detailed descriptions of embodiments of the invention. However, techniques, systems, and operating structures in accordance with the invention may be embodied in a wide variety of forms and modes, some of which may be quite different from those in the disclosed embodiments. Also, the features and elements disclosed herein may be combined to form various combinations without exclusivity, unless expressly stated otherwise. Consequently, the specific structural and functional details disclosed herein are merely representative. Yet, in that regard, they are deemed to afford the best embodiments for purposes of disclosure and to provide a basis for the claims herein, which define the scope of the invention. It should also be noted that, as used in the specification and the appended claims, the singular forms "a", "an", and "the" include plural referents unless the context clearly indicates otherwise.

Use of the term "exemplary" means illustrative or by way of example, and any reference herein to "the invention" is not intended to restrict or limit the invention to the exact features or steps of any one or more of the exemplary embodiments disclosed in the present specification. Also, repeated use of the phrase "in one embodiment," "in an exemplary embodiment," or similar phrases do not necessarily refer to the same embodiment, although they may. It is also noted that terms like "preferably," "commonly," and "typically," are not used herein to limit the scope of the claimed invention or to imply that certain features are critical, essential, or even important to the structure or function of the claimed invention. Rather, those terms are merely intended to highlight alternative or additional features that may or may not be used in a particular embodiment of the present invention.

For exemplary methods or processes of the invention, the sequence and/or arrangement of steps described herein are illustrative and not restrictive. Accordingly, it should be understood that, although steps of various processes or methods may be shown and described as being in a sequence or temporal arrangement, the steps of any such processes or methods are not limited to being carried out in any particular sequence or arrangement, absent an indication otherwise. Indeed, the steps in such processes or methods generally may be carried out in various different sequences and arrangements while still falling within the scope of the present invention.

The present invention may be implemented by a software application running on a device, such as a mobile device (e.g., a mobile phone, tablet). The device preferably has a display screen, a microphone, a speaker, a camera capable of recording video, a flashlight or flash for the camera, and non-transitory memory. Journal entries may be stored in the memory of the device on which they are recorded and/or at a location separate and/or remote from the device, such as a central server, or an on-line database.

The software application may allow the user of the device to record an audio and/or video journal entry only when the software application determines that the user is looking, or likely looking, at themselves in a mirror. The software application may be run by a user of the device (also referred to herein as a patient), individually or in collaboration with a clinician.

The software application may use computer vision (machine learning) real-time analysis of video recorded by the device camera to verify that the user is in front of a physical mirror. The software application may be implemented as an Augmented Reality ("AR") software application. Face image object detection is available in popular AR development tools like ARCore and ARKit. Image detection components, multiple image layer detection, and smartphone image object geometry extract may be implemented using low level Computer Vision tools like OpenCV.

When initiated, the software application may provide relevant prompts to the user. For example, the software application may cause the device on which it is running to display the question, "How happy are you with your body, and why do you feel that way?" Prompts may also be customized for each particular user. For example, a clinicians may add to the software application a recorded prompt that addresses the patient individually (e.g., by mentioning the patient's name) and asks the patient a question specific to the patient. For example, a clinician treating a patient may record a prompt that is relevant to a condition the patient is experiencing.

In one embodiment, recorded journal entries may be accessed by one or more persons other than the patient. For example, a patient may grant to a clinician access to one or more journal entries via a secure online data repository and clinician portal. The journal entries may be played or viewed by a clinician. The software application may also may also provide an option for a clinician to respond to one or more patient journal entries, such as by recording one or more text, audio, and/or video messages.

To encourage the user to look at themselves in a mirror when they are recording a journal entry, the software application may be configured to record a journal entry only when the software application determines that the user is standing in front of a physical mirror. In accordance with one embodiment of the present invention, a user may launch the software application by, for example, selecting an icon on a display screen of a device on which the software application is installed. Once the software application launched, the user may enter an input requesting to record a journal entry.

The software application may then activate the video camera of the device. Video captured by the video camera may be displayed on the display screen of the device. The software application may analyze the captured video in real-time. For example, the software application may use machine learning or other mathematical techniques to analyze the captured video. The user then may situate themselves in front of a mirror in a position that allows them to see both themselves and their device while the video is captured. Alternatively, the user may situate themselves in front of a mirror before or during initiation of the software application and remain so situated while the video is captured.

The user may view the captured video on the display screen of the device and adjust themselves so both their face and phone are captured. The software application may detect the image of a human face and/or body in the captured video through computational techniques such as the Haar Cascade object detection algorithm and/or Convolutional Neural Networks. Once the image of a face and/or body is detected, additional analysis may be applied to determine if the image is produced by a mirror.

In one embodiment, the rectangular shape of a mobile device may be detected in captured video using computational techniques such as the Haar Cascade object detection algorithm and/or Convolutional Neural Networks. The location and orientation of the device capturing the video may indicate that the device camera is pointed at a mirror.

In low light conditions or other circumstances which make video analysis difficult, the device flash light may be activated for a short period of time, and the software may detect an increase in the contrast between the highest light intensity and lowest light intensity in the captured video. If the contrast between the highest light intensity and lowest light intensity increases above a predetermined threshold, the software application may determine that the user is facing a mirror.

Once the software application determines that the user is facing a mirror, the software application may cause recorded prompts to be played. For example, questions about how the user feels may be displayed on the device display screen, or may be played by the device speaker. The prompts may be customized by the user and/or by the software application publisher.

Because it can be difficult to escape the distractions of digital media that may be presented by other applications on a device, the software application or other software on the device may restrict certain functions that the user may access at or around the time they are recording a journal entry. For, example, the user may be prevented from opening a journal entry session in a new browser tab. Additionally or alternatively, the user may be prevented from receiving notifications from or checking social media application or email when recording of a journal entry has been initiated and until recording has been completed.

As described above and in more detail below, the software application may use one or methods to determine whether the user of the software application is facing a mirror. Referring to FIGS. 1A-1F, six images of a rear facing mobile device are depicted. Like the vast majority of mobile devices, the pictured device is rectangular. The sides are identified as top (a), bottom (b), left (c) and right (d). Each image shows the mobile device as it might appear when oriented in a particular position. Although the device is rectangular, its image is not rectangular in any of the pictured images with the exception of the center image. This is because of perspective—the spatial orientation of a person's eyes relative to a perceived object skews perceived geometry: things that are farther away seem smaller, just as the lines of a long, straight highway recede to a point on the horizon. If the geometry of a detected mobile device image object quadrilateral is not rectangular, then the mobile device image object is not produced by a mirror reflection.

Computer vision line (edge) detection and line relationship analysis allows for the extraction of the quadrilateral geometry of an image object. The extracted geometric data may provide the relative lengths of sides a, b, c and d as shown in the illustration. The software application may be configured so that, the user may only record a journal entry if the detected geometry of the mobile device image object quadrilateral is rectangular. A rectangular geometry indicates that the back surface of the mobile device is parallel or generally parallel to the mirror surface and, in that orientation, the camera would be pointed directly at the mirror.

Additionally or alternative, the software application may detect whether one or more sides of the image object rectangle are parallel to the video image frame. All mobile device camera frames are aligned in parallel with the rectangular geometry of almost all mobile devices. For example, as a mobile device is rotated along an axis perpendicular to a mirror they are pointing the device at, the camera frame and device mirror image rotate in tandem.

Figure 2A:
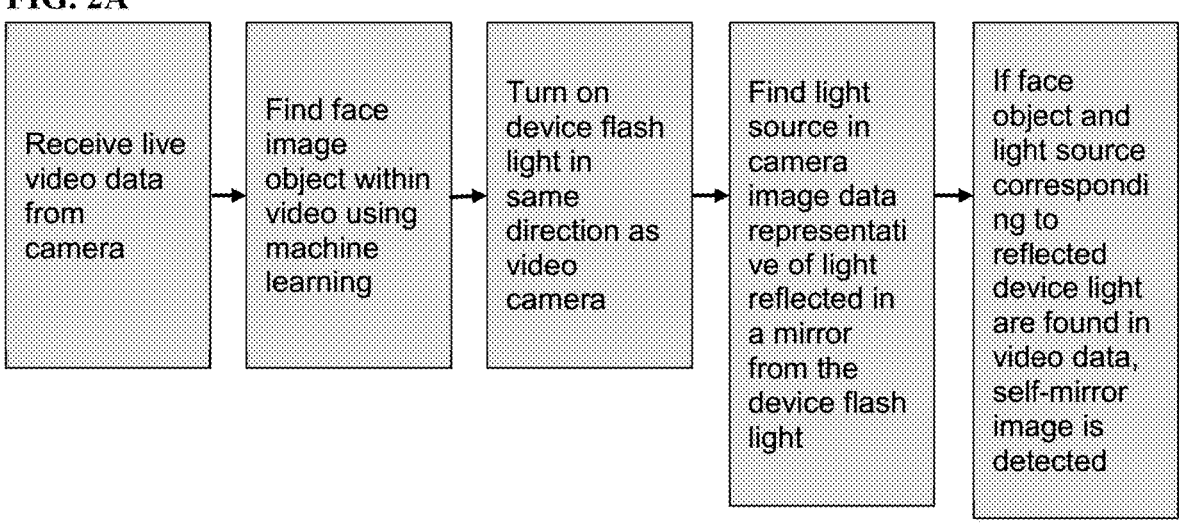
FIGS. 2A-2C depict methods of self mirror image detection by reflection of device light source detected by device camera data.
Figure 2B:
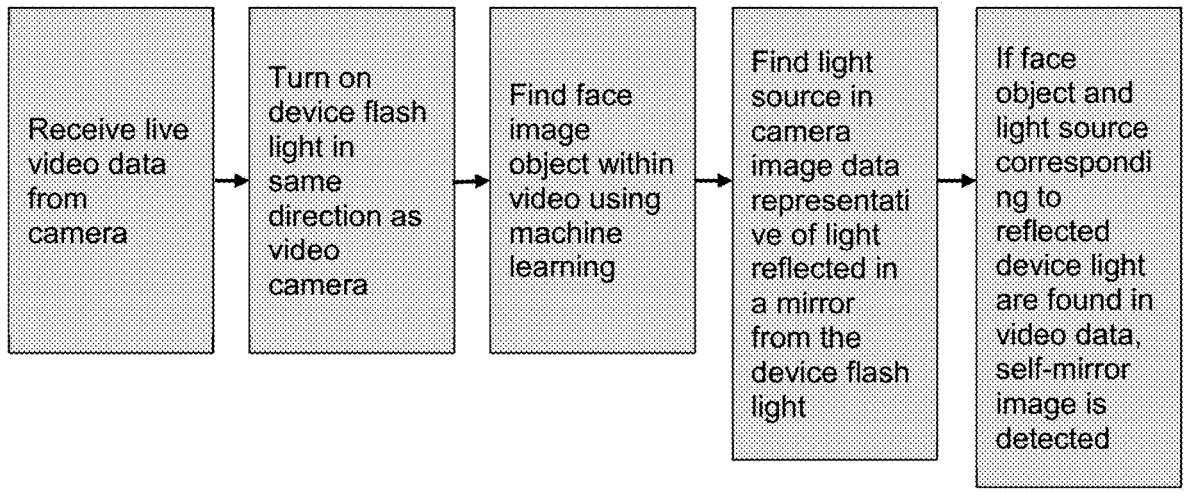
Figure 2C:

Referring to FIGS. 2A-2C, in contrast to passive video image analysis, self mirror images may be detected actively with a rear facing mobile device camera flash or flash light, typically a white LED. The device light may be activated for a brief period of time, such as one second, and then deactivated. A video image captured while the light is on may be compared to a video image captured immediately before the light is activated or immediately after the light is deactivated. If the difference between the total light exposure intensity of the image when the light is on as compared to when the light is off, is greater than a predetermined threshold, the software application may determine that the device camera is directed toward a mirror, and a "self mirror image" is being captured.

Additionally, the location of the reflected camera light within the image frame can be determined by isolated high light intensity pixels that greatly change in light intensity value. See FIG. 2C, element (a). This flash light image object can be compared to the position of detected face image object (FIG. 2C, element (b)) and/or mobile device image object to further ensure the detected light change is indicative of a self mirror image. For example, the light image object should be superimposed on the mobile device image object and should not be immediately above the face image object if a self mirror image is detected.

FIGS. 2A and 2B are flow charts that illustrate exemplary processes by which active light detection can be used to determine presence of a self mirror image. The process is probabilistic and multifaceted. Although face image detection is an integral component, it can take place before or after active light detection. In addition to the illustrated process steps, additional modes of analysis can be added to increase accuracy of self mirror image detection. Because face image detection is itself probabilistic, it is not a requirement for self mirror image detection. For example, if face detection is 25% likely, mobile device image detection is 85% likely, rectangular mobile device image shape is 80% likely and device flash light image superposition in mobile device image object is 80% likely then the cumulative likelihood of self mirror image detection may still cross a predetermined threshold indicating successful self mirror image detection.

Figure 3A:
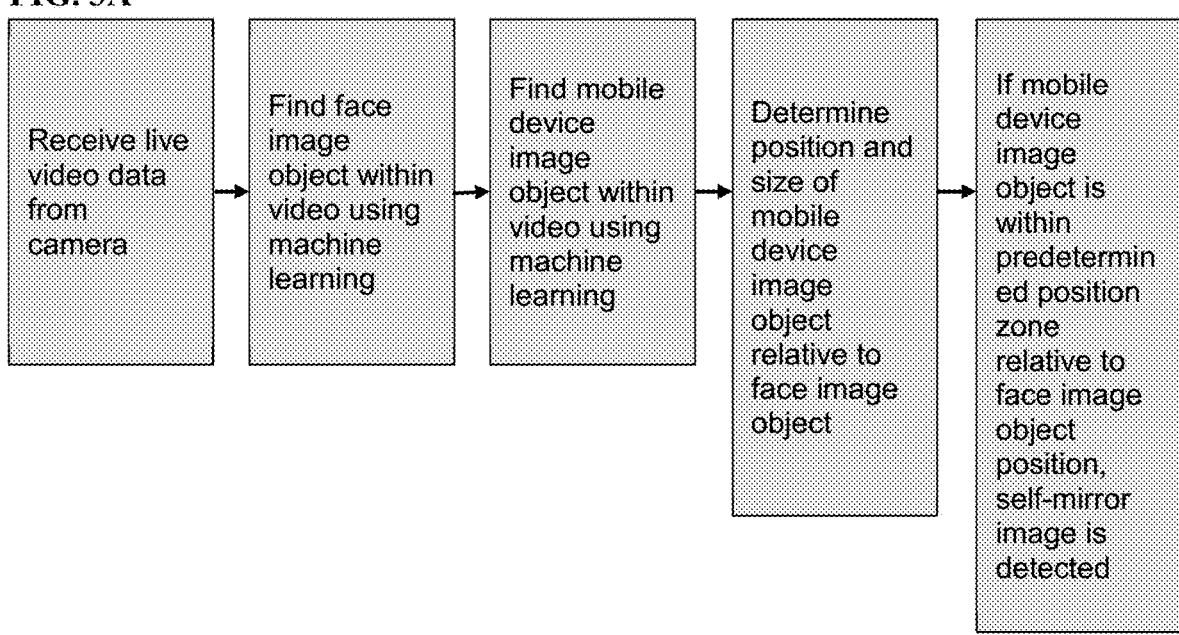
FIGS. 3A-3C depict methods of self mirror image detection by the position of a detected mobile device image object relative to a detected face image object.
Figure 3B:
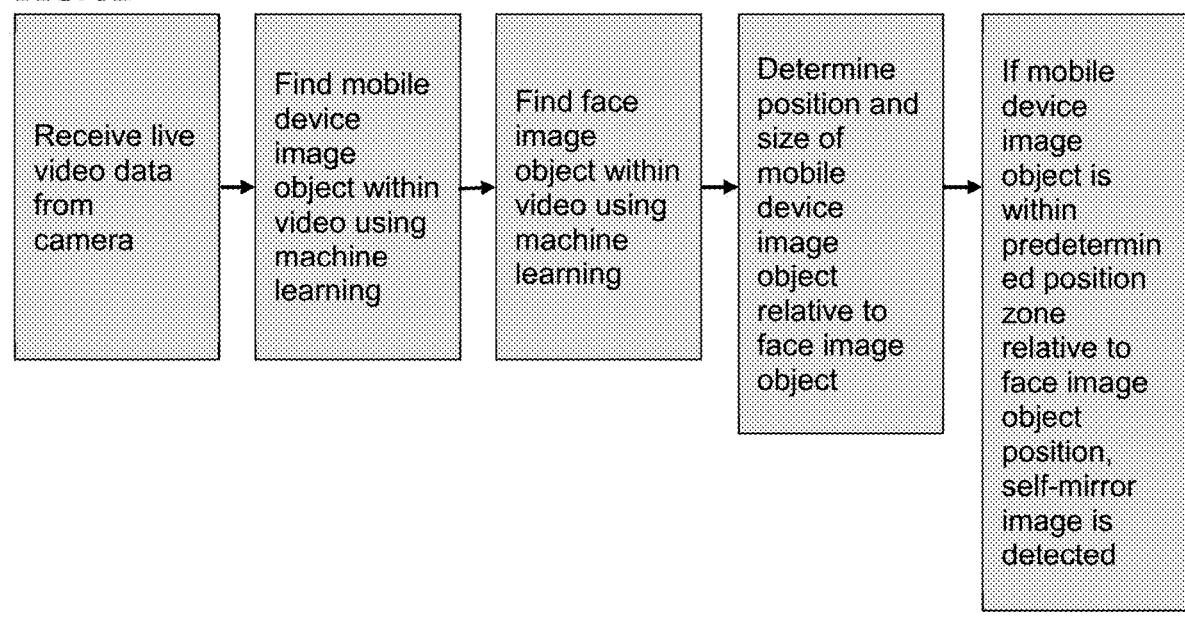
Figure 3C:
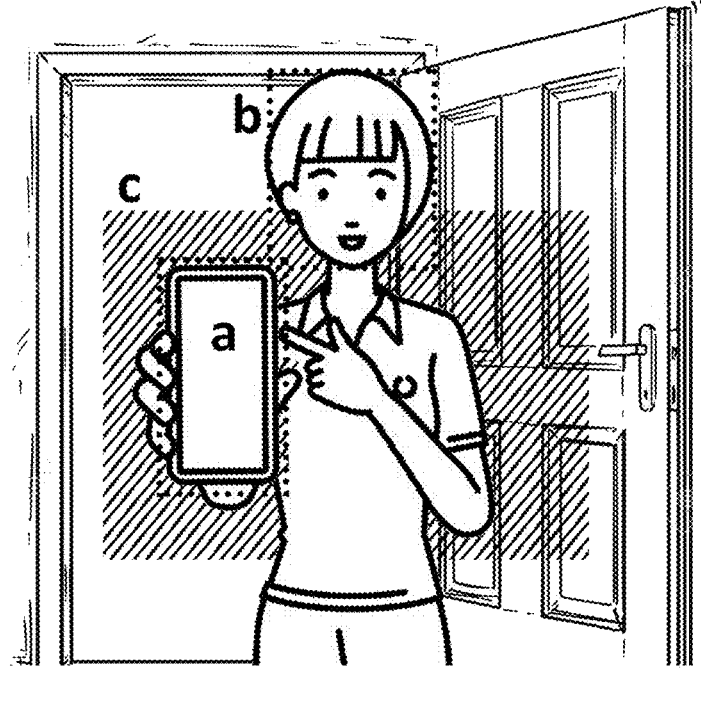

The sequence of detection methods can be varied. A face image object may be detected before the device (or other video camera producing the video data being analyzed) image object is detected or afterwards. Computer vision analysis of the face for characteristics indicative of a self mirror image may be added to other methods or used alone. For example, an image of the user may be accessed by a computer vision analysis application and compared to the face image object detected in live video. If the pre-obtained user face image matches the detected image object face (facial recognition), self mirror image detection is more likely since a self mirror image will produce a face image object similar to the user. More specifically, if the pre-obtained user fascia image indicated asymmetrical characteristics as determined by computer vision analysis, this asymmetry (such as a large scar on one side of the face) can also be used for self mirror image detection. In a self mirror image, the position of the asymmetry would be reversed (mirrored), if the video image captured a face image object generated by a large print poster photo of the user, the asymmetry would not be reversed Referring to FIGS. 3A-3C, the positions in which a person might hold a mobile device when pointing the mobile device at a mirror are predictable and physically constrained by human anatomy. These constraints and predictable behaviors may be used to generate a zone in which a mobile device image object might appear relative to a face image object and vice versa in captured video images. Once a face image object (FIG. 3C, element (b)) and mobile device image object (FIG. 3C, element (a)) are found in video, their X/Y coordinate position relationships are cross referenced with this constrained zone (FIG. 3C, element (c)) of anatomical possibility and likely behavior. If the device image object is within this zone, the likelihood of self mirror image detection is increased, possibly conclusively. FIGS. 3A and 3B are flowcharts that illustrate alternative exemplary processes by which this determination may occur.

Figure 4A:
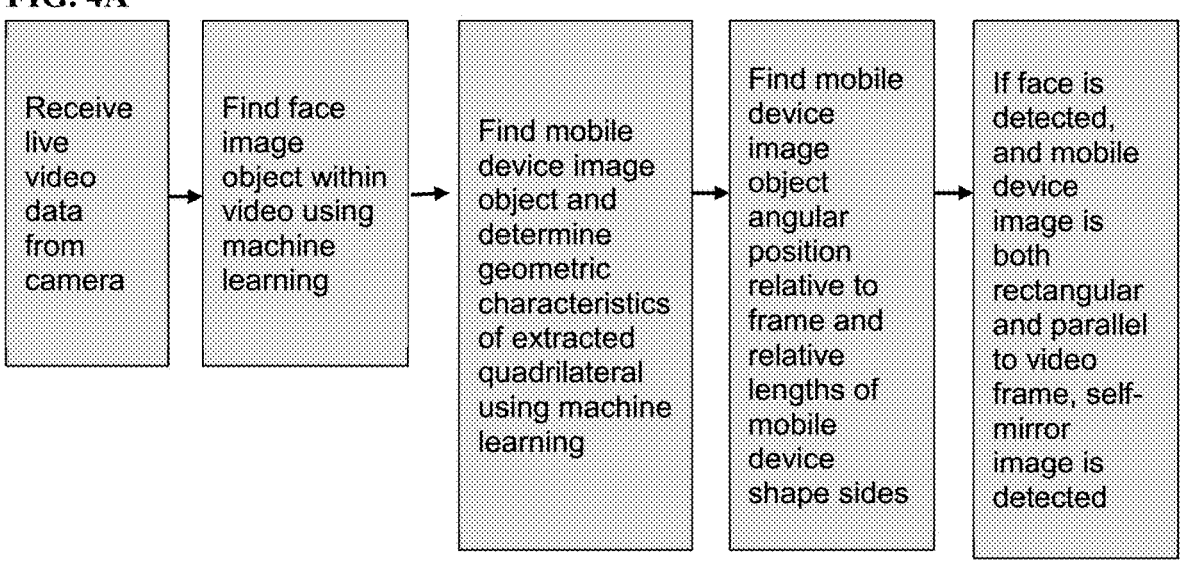
FIGS. 4A-4C depict methods of self mirror image detection by detecting device angular position and geometry of device image.
Figure 4B:
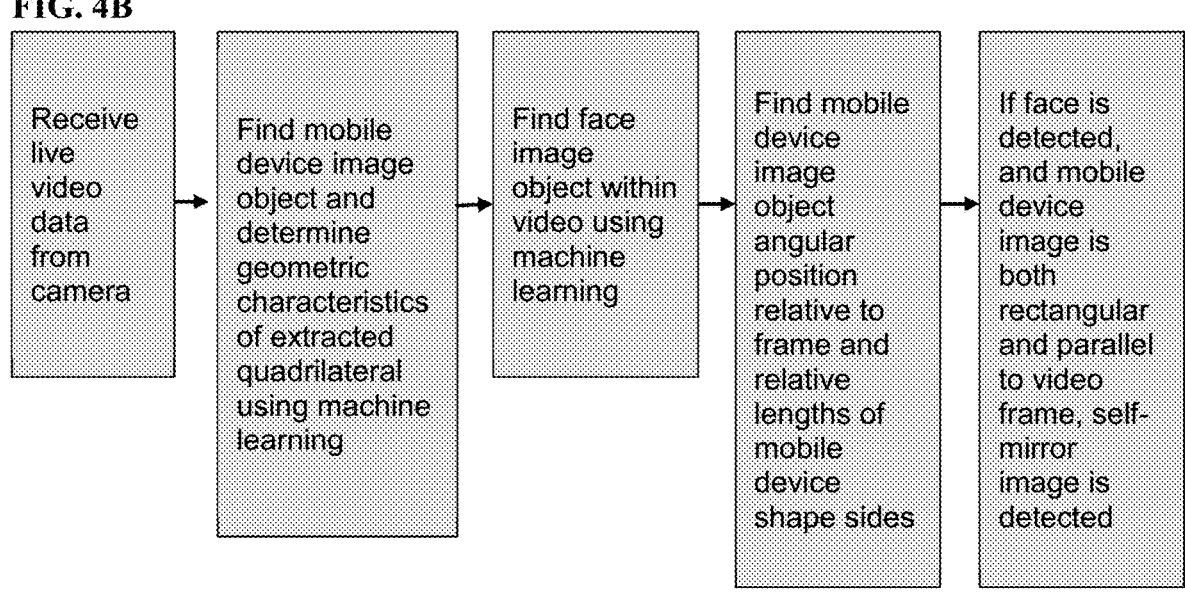
Figure 4C:
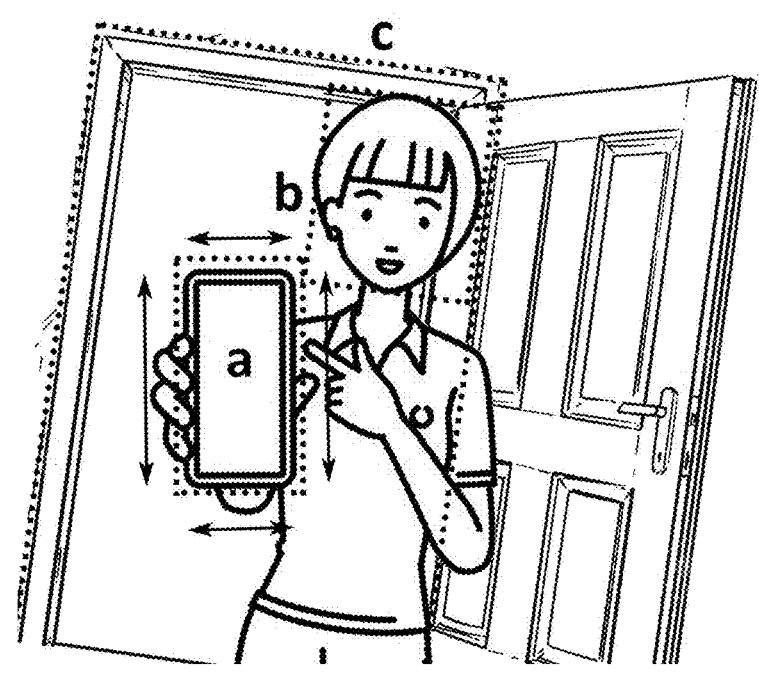

Referring to FIGS. 4A-4C, because the overwhelming majority of mobile devices are rectangular, the shape of a mobile device is predictable. In addition, the exact model of the mobile device being used may be known in which case, the exact dimensions of the device can further increase accuracy of mobile device image object detection and geometry extraction. Because the software application may require the mobile device camera sensor to be parallel or generally parallel with a mirror in order to capture a reflected image of itself, a mirror image of the mobile device in use may always have a rectangular geometry (FIG. 4C, element (a)). In addition, the sides of the mobile device image object rectangle may always be parallel with the sides of the video camera frame (FIG. 4C, element (a)). Detection of these two circumstance—rectangular geometry and parallel orientation to image frame—may indicate an increased likelihood of self mirror image detection. These analytic methods can be used together, separately, and/or in combination with other illustrated methods such as a positional relationship between device image object and face image object. FIGS. 4A and 4B are flowcharts illustrating alternative exemplary methods that may be used in the process of self mirror image detection.

Figure 5A:
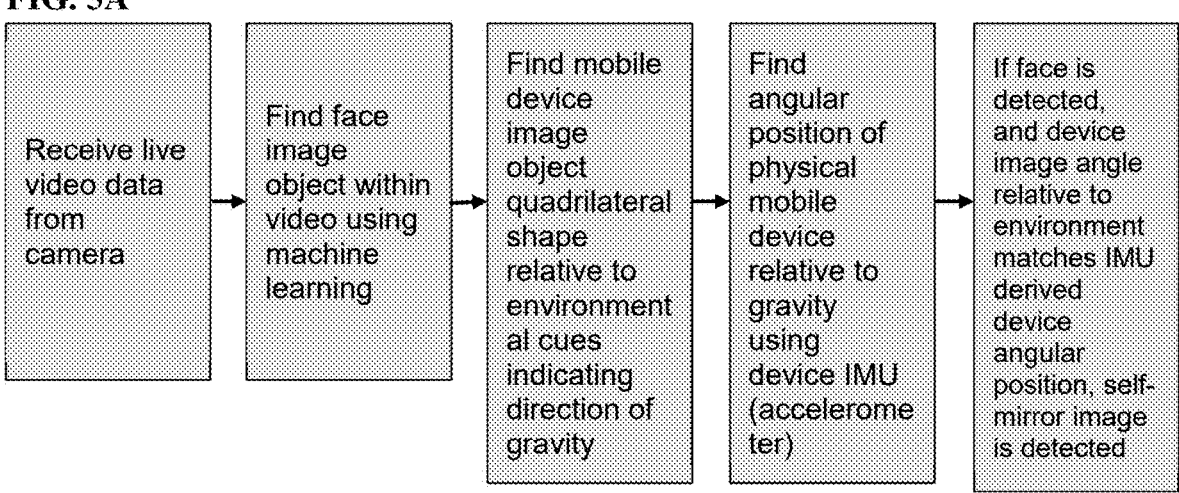
FIGS. 5A-5C depict methods of self mirror image detection by detecting a device image angular position and the device inertial measurement unit (IMU) angular position.
Figure 5B:
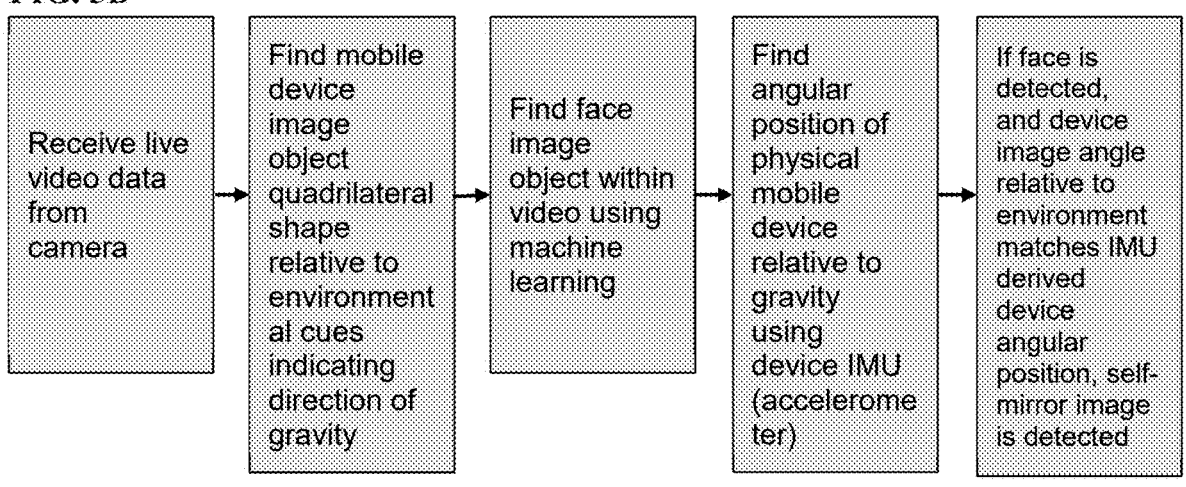
Figure 5C:
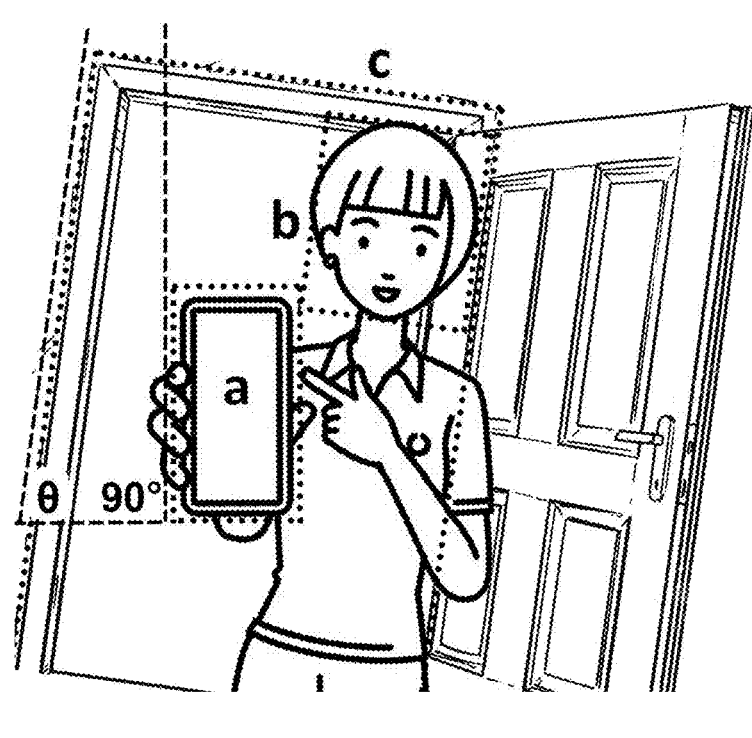

Referring to FIGS. 5A-5C, a mobile device may contain an inertial measurement unit ("IU"), which may comprise an accelerometer or stand-alone accelerometer. This IMU may be used by the mobile device to determine, for example, the screen orientation to display when the device is rotated. The mobile device IMU may be a three dimensional sensor which indicates acceleration along three axes: x, y and z. The IMU may be used to determine the mobile device's angular position relative to gravity.

Once a mobile device image object is detected within a captured video image, it may be possible to determine the device image object's angular position using cues extracted from the surrounding video image. For example, roads, telephone lines, floors, ceilings, fences, tables display geometries that are perpendicular to the force of gravity. Walls, door frames, tree trunks, human faces, lamps and buildings display geometries that are parallel to the force of gravity. See FIG. 5C, elements (b) and (c). Even if the identity of these environmental objects cannot be determined using simple computer vision algorithms, the confluence of parallel and perpendicular lines which constitute these image object geometries can be used to determine the angular position of the force of gravity relative to the video image frame. Since the mobile device image object is typically aligned with the video image frame (FIG. 5C, element (a)), the environmental cues indicating the position of gravity can be used to derive the angular position of the mobile device image object relative to gravity. The video image derived device angular position can be compared to the accelerometer derived angular position. If the video image derived angular position matches the accelerometer derived angular position the likelihood of self mirror image detection is increased. FIGS. 5A and 5B are flowcharts illustrating alternative exemplary methods that may be used in the process of self mirror image detection.

Figure 6A:
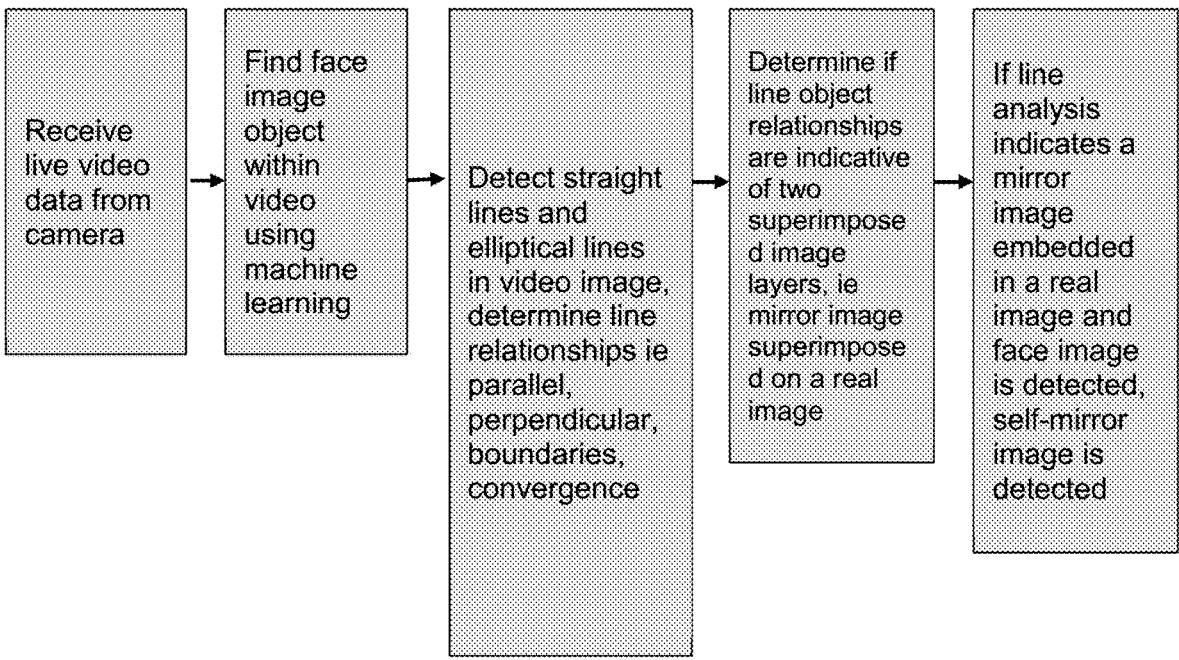
FIGS. 6A-6C depict methods of self mirror image detection by detecting multiple image layers.
Figure 6B:
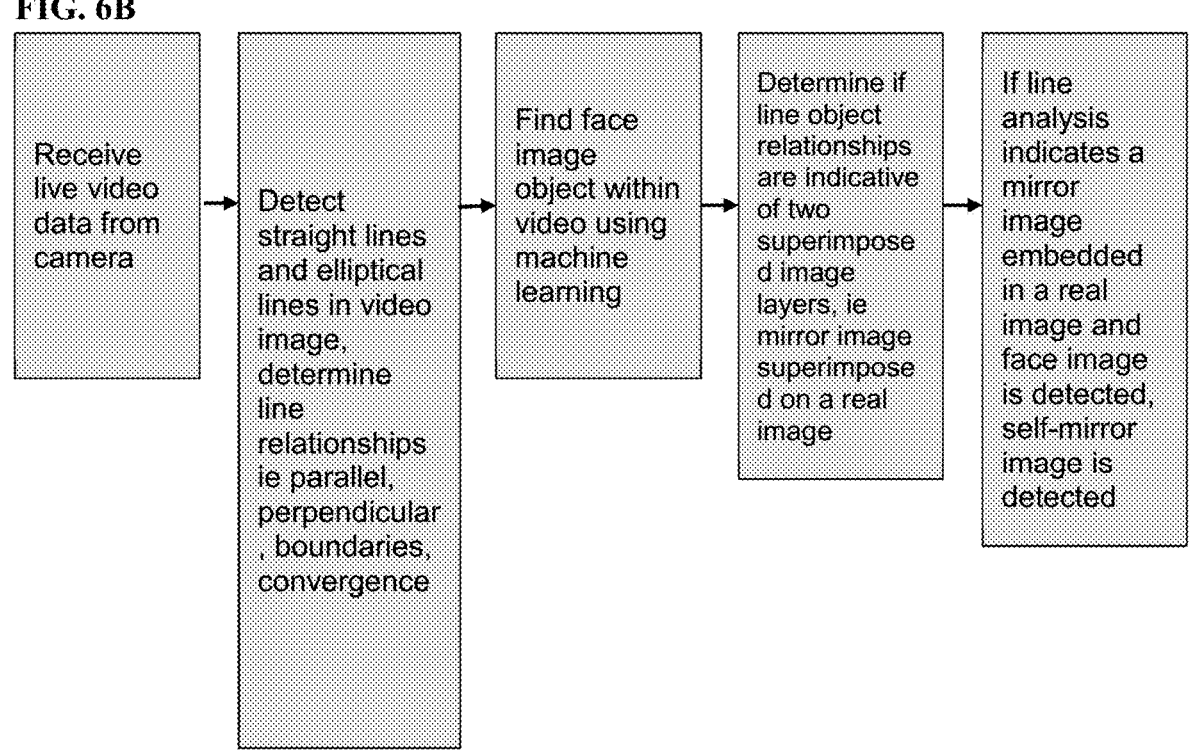
Figure 6C:
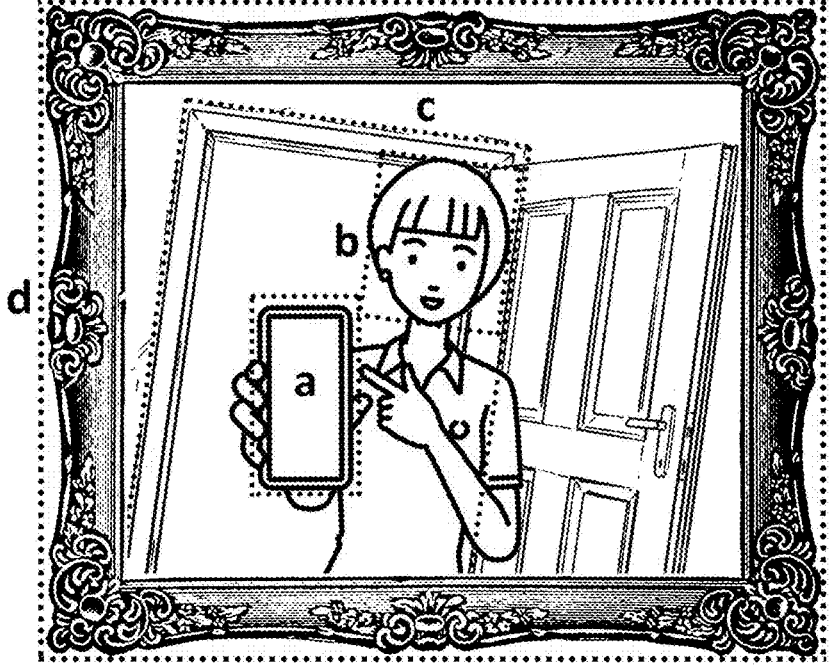

Referring to FIGS. 6A-6C, an image of an environment can be characterized by gradients in perspective, for example the width of a road decreases gradually as it recedes towards a horizon. A human viewer can perceive distance and three dimensional spatial relationships in a two dimensional landscape. Similarly, computer vision can use image object detection and analysis of detected lines (edges) to predict continuance and uniformity in image environmental perspective. A poster or photograph of a landscape mounted on a wall which is itself then photographed creates two image layers and thus two image perspectives. Similarly, a video image of a mirror generates two image layers and thus two image perspectives with associated environmental geometric characteristics. The edge of a mirror creates a boundary between the reflection image layer and real image layer. Moreover, the image layer boundary cuts off the reflection image layer.

Machine learning can be used to detect the presence of two image layers and determine the locations of a boundary between image layers. This is done through line (edge) detection, image object detection and analysis of the relationship between detected lines and objects. The detection and location of multiple image layers can be combined with other image analysis to detect a self mirror image. For example, if a face image object (FIG. 6C, element (b)) and mobile device image object (FIG. 6C, element (a)) are located within a central image layer which is cut off by a peripheral image layer (FIG. 6C, element (d)), a self mirror image is likely. FIGS. 6A and 6B depict flowcharts that illustrate how exemplary methods can be used in the process of self mirror image detection.

Figure 7:
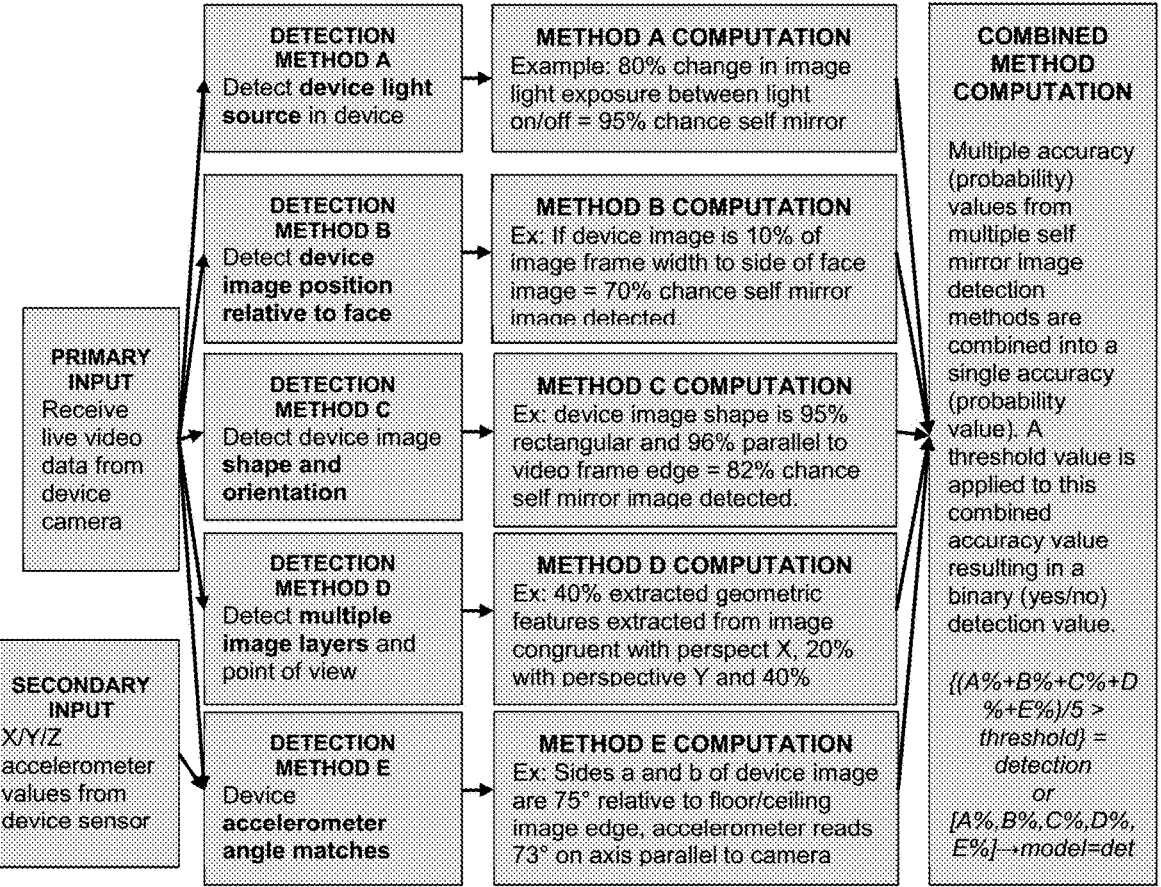
FIG. 7 depicts methods of self mirror image detection by combining analytic methods.

Referring to FIG. 7, combining the self mirror image detection methods, such as the methods discussed above, can greatly increase the accuracy of self mirror image detection. The combination can be considered cross verification. Some of the methods discussed may be probabilistic in nature. In a preferred embodiment, multiple methods may be used and resulting accuracy values may be combined in a weighted algorithm. For example, the probabilistic determination resulting from two or more methods may be averaged to arrive at a single resulting number that can be compared to a predetermined threshold amount.

The algorithm used to combine the results may employ machine learning techniques such as neural networks. In the case of trained model machine learning, a normalized (0.1, 0.748 etc.) training data set may be gathered by applying the computational methods described in the methods above to video data, including "true" video data portraying self mirror images, and "false" video data portraying something else (actual non-mirror footage of people and device etc). The normalized probabilistic results of the computational methods (model "features") may be paired with the actual true/false ("1.0","0.0") presence of a self mirror image ("output") and fed into a training algorithms for creation of machine learning models such as neural networks. This model may incorporate information about the relationship between different methods in terms of predicting the presence of a self mirror image.

Once a binary "yes or no" estimation of self mirror image presence is calculated, a number of software and hardware actions may be triggered. For example, the ability to enter a new journal entry may be unlocked. Other actions might be triggered instead or as well. For example, an alert may be sent to the patient's clinician, such as by text message, an email, message, or different type of message sent over the internet. The mobile device's speaker may be silenced and the device's vibration motor may be turned on instead. Background notifications on the mobile device may be suppressed. The detection of self mirror image in video data may also be used for security purposes as an authentication method to access private information.

Figure 8:
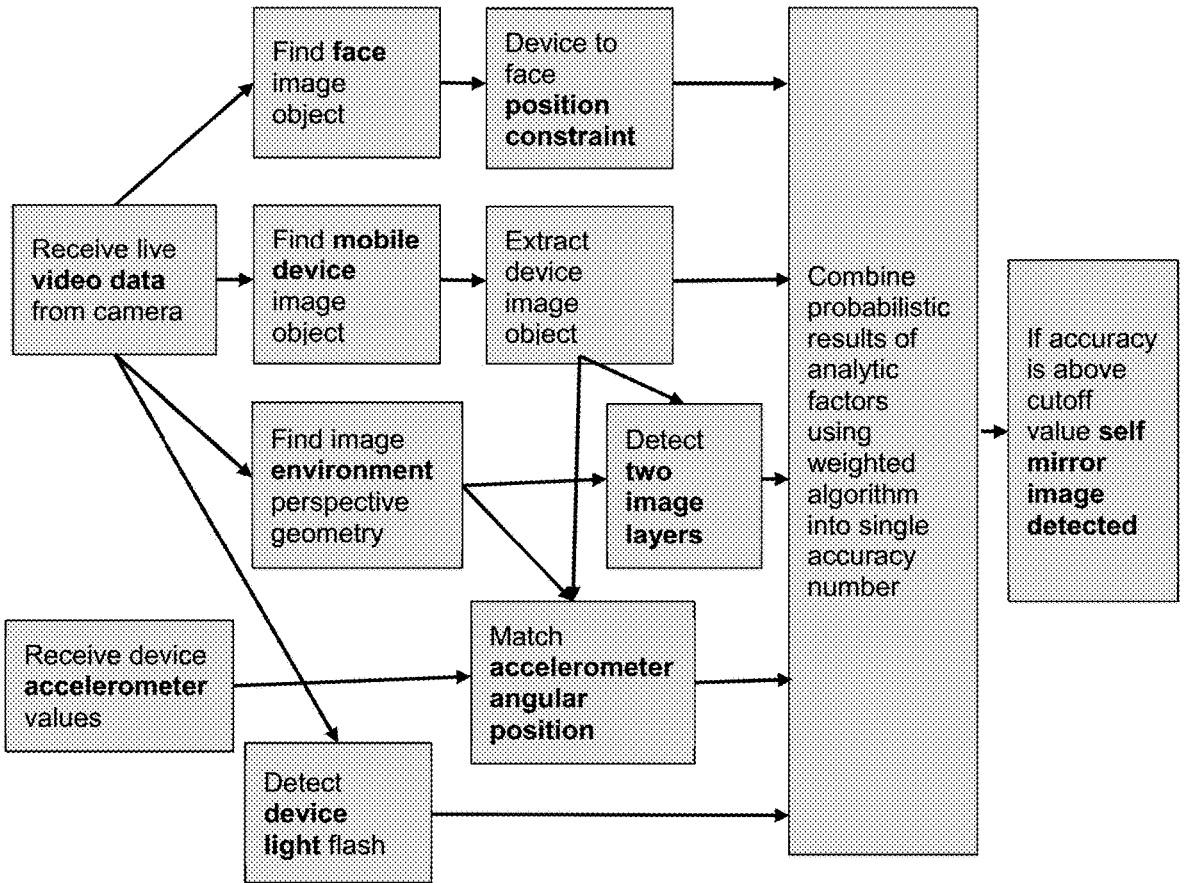
FIG. 8 depicts an exemplary methods of self mirror image detection.

FIG. 8 depicts an example of multiple methods implemented as described broadly above with reference to FIG. 7.

While the invention has been described in detail with reference to embodiments for the purposes of making a complete disclosure of the invention, such embodiments are merely exemplary and are not intended to be limiting or represent an exhaustive enumeration of all aspects of the invention. It will be apparent to those of ordinary skill in the art that numerous changes may be made in such details, and the invention is capable of being embodied in other forms, without departing from the spirit, essential characteristics, and principles of the invention. Also, the benefits, advantages, solutions to problems, and any elements that may allow or facilitate any benefit, advantage, or solution are not to be construed as critical, required, or essential to the invention. The scope of the invention is to be limited only by the appended claims.

What is claimed is:

1. A device for journaling comprising:
   a non-transitory memory;
   a display;
   a camera comprising an image frame and capable of capturing video;
   one or more processors coupled to the non-transitory memory; and
   executable software instructions stored on the non-transitory memory, which when executed by the processor configure the device to:
   initiate capture of video by the camera,
   detect a face image object within the video,
   detect a device image object within the video,
   determine an extracted quadrilateral of the device image object,
   detect an angular position of the device image object relative to the image frame and length of device shape sides, determine self-mirror image detection if the face image object is a human face, if the extracted quadrilateral is rectangular and if the angular position is parallel to the image frame, and display on the device an indication of self-mirror image detection.

2. The device of claim 1, further configured to verify if the device is facing a mirror.

3. The device of claim 1, further configured to verify if a user of the device is facing the mirror.

4. The device of claim 3, further configured to verify the user of the device is facing the mirror via machine learning real-time analysis of the video captured by the camera.

5. The device of claim 1, wherein the indication indicates the beginning of a journal entry.

6. The device of claim 1, further configured to provide access to the video captured by the camera by a person other than a user of the device.

7. The device of claim 1, further configured to transmit the video captured by the camera to a repository.

8. The device of claim 1, further configured to activate a flash on the device.

9. The device of claim 8, further configured to detect an increase in contrast in the video captured by the camera caused by the flash and determine if the increase is above a predetermined threshold.

10. The device of claim 1, further configured to restrict one or more features of the device when journaling.

11. A device for journaling comprising:
a non-transitory memory;
a display;
a camera capable of capturing video;
an inertial measurement unit capable of sensing the direction of a gravitational force;
one or more processors coupled to the non-transitory memory; and
executable software instructions stored on the non-transitory memory, which when executed by the processor configure the device to:
initiate capture of video by the camera,
detect a face image object within the video,
detect a device image object within the video,
detect one or more surrounding object cues within the video,
determine an extracted quadrilateral of the device image object,
determine a first angular position of the device image object relative to the one or more surrounding object cues,
determine a second angular position of the device relative to the direction of the gravitational force via the inertial measurement unit,
determine self-mirror image detection by comparing the first angular position to the second angular position, and
display on the device an indication of self-mirror image detection.

12. The device of claim 11, further configured to verify if the device is facing a mirror.

13. The device of claim 11, further configured to verify if a user of the device is facing the mirror.

14. The device of claim 13, further configured to verify the user of the device is facing the mirror via machine learning real-time analysis of the video captured by the camera.

15. The device of claim 11, wherein the indication indicates the beginning of a journal entry.

16. The device of claim 11, further configured to provide access to the video captured by the camera by a person other than a user of the device.

17. The device of claim 11, further configured to transmit the video captured by the camera to a repository.

18. The device of claim 11, further configured to activate a flash on the device.

19. The device of claim 18, further configured to detect an increase in contrast in the video captured by the camera caused by the flash and determine if the increase is above a predetermined threshold.

20. The device of claim 11, further configured to restrict one or more features of the device when journaling.

21. A mobile device for journaling a user comprising:
a camera configured to capture video;
one or more processors; and
a non-transitory memory having executable software instructions stored thereon, which when executed by the processor configure the mobile device to:
receive video data from the camera;
detect a device image object, and face image object within the video data;
calculate a probability of detection for each:
a device image position from device image object,
a face image of the user from face image object, and
a device image shape and orientation from device image object;
determine a combined probability from each probability of detection;
compare a predetermined threshold value to the combined probability, wherein the comparison determines portrayal of the user or non-portrayal of the user in a mirror;
initiate journaling if the comparison determines portrayal of the user.

22. The mobile device of claim 21, wherein detection is performed by machine learning.

23. The mobile device of claim 21, further comprising a inertial measurement unit adapted to provide an angular position of the mobile device relative to gravity, wherein the angular position is compared to the device image shape and orientation.

24. The mobile device of claim 21, further comprising a light source configured to provide light in the same direction as the camera, wherein light in the video data is detected, a probability of detection of light from the light source is calculated and combined with the combined probability.

* * * * *